United States Patent [19]

Adams

[11] 4,059,116
[45] Nov. 22, 1977

[54] SYNCHRONOUS PACEMAKER WITH UPPER RATE STABILIZATION AND METHOD OF USE

[75] Inventor: John M. Adams, Minneapolis, Minn.

[73] Assignee: Medtronic, Inc., Minneapolis, Minn.

[21] Appl. No.: 648,352

[22] Filed: Jan. 12, 1976

Related U.S. Application Data

[63] Continuation of Ser. No. 530,799, Dec. 9, 1974, abandoned.

[51] Int. Cl.² .............................................. A61N 1/36
[52] U.S. Cl. ............................................. 128/419 PG
[58] Field of Search ............ 128/419 PG, 419 R, 421, 128/422, 423

[56] References Cited

U.S. PATENT DOCUMENTS

| | | | |
|---|---|---|---|
| 3,253,596 | 9/1966 | Keller, Jr. | 128/419 PG |
| 3,391,697 | 7/1968 | Greatbatch | 128/419 PG |
| 3,648,707 | 3/1972 | Greatbatch | 128/419 PG |
| 3,669,120 | 6/1972 | Nielsen | 128/419 PG |
| 3,807,410 | 4/1974 | Wall et al. | 128/419 PG |
| 3,903,897 | 9/1975 | Woolons et al. | 128/419 PG |
| 3,920,024 | 11/1975 | Bowers | 128/419 PG |

*Primary Examiner*—William E. Kamm
*Attorney, Agent, or Firm*—Harry W. Barron; Joseph F. Breimayer

[57] ABSTRACT

A synchronous artificial cardiac pacemaker having a first electrode adapted to be coupled to the ventricle of a patient's heart to pick up ventricular heart activity and to conduct stimulating pulses to the ventricle, a second electrode adapted to be coupled to the atrium of a patient's heart to pick up atrial heart activity and a pulse generator powered by a battery power source and coupled to the two electrodes and to an indifferent electrode. The pulse generator includes a timing circuit that, in the absence of any heart activity for a predetermined maximum time interval, produces stimulating pulses at a lower base pacing rate. The pulse generator also includes a first sensing circuit coupled to the ventricular electrode and a reset circuit coupled to the timing circuit. Natural ectopic heart beats indicative of ventricular activity are picked up by the ventricular electrode, sensed by the sensing means and applied to the reset circuit which resets the operation of the timing circuit. A second sensing circuit is coupled to the atrial electrode and, through a memory circuit and a time delay circuit to the timing circuit. In cases where atrial heart activity is picked up, the sensing circuit produces a signal that sets the memory circuit and after a time delay, triggers the timing circuit into producing a stimulating pulse for application to the ventricle in synchronism with the natural atrial contraction of the heart. In cases where the atrial rate becomes excessive, the pulse generator circuit operates through an upper rate limit circuit coupled to the timing circuit and the operation of the memory circuit to synchronously pace the ventricles at an average rate not exceeding the upper rate of the timing circuit.

17 Claims, 8 Drawing Figures

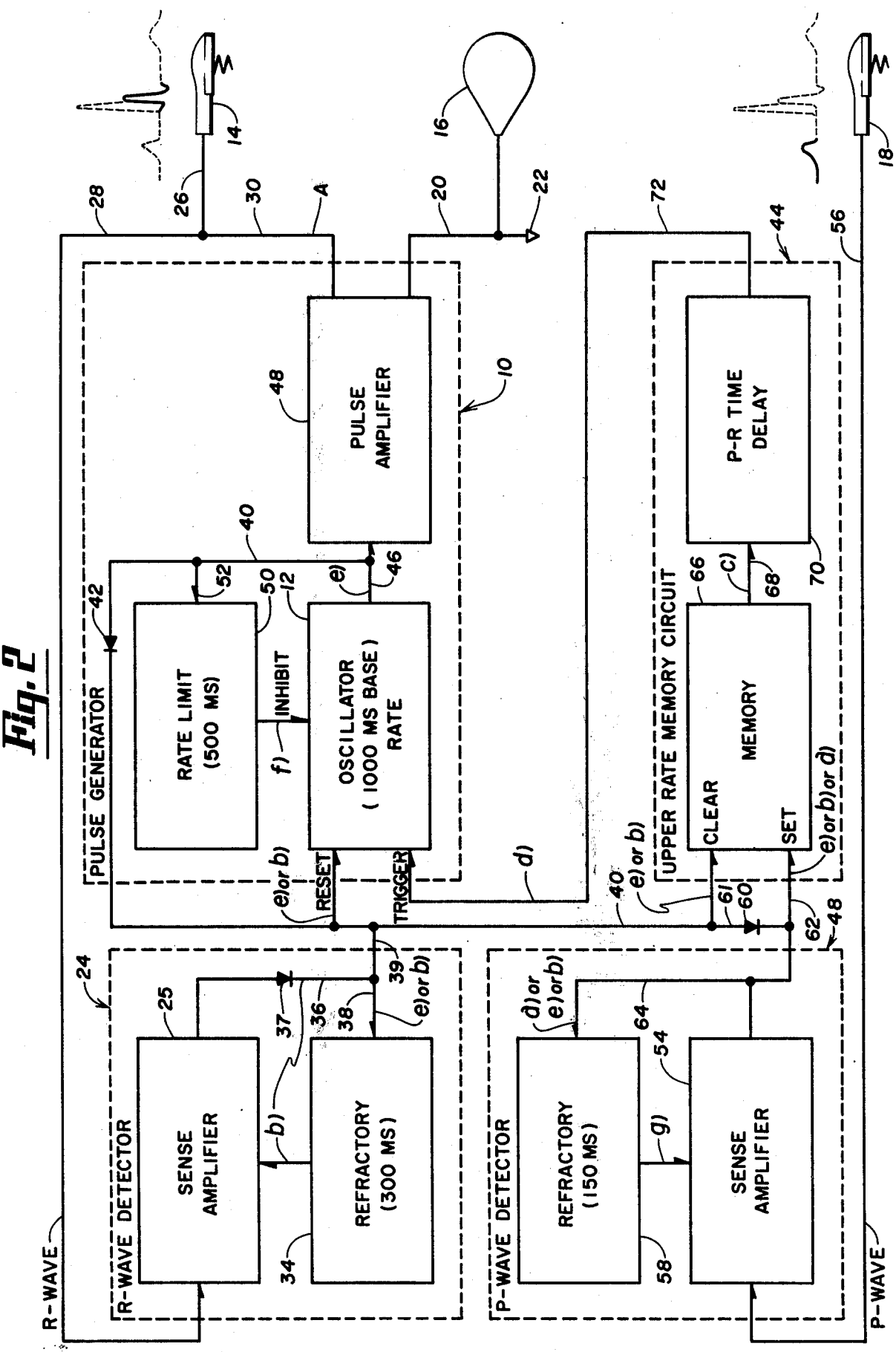

SYNCHRONOUS PACEMAKER WITH UPPER RATE STABILIZATION AND METHOD OF USE

This is a continuation of application Ser. No. 530,799, filed Dec. 9, 1974, and now abandoned.

BACKGROUND OF THE INVENTION

1. Field of the Invention

This invention relates to artificial cardiac pacemaker and more particularly, to a cardiac pacemaker which may or may not be implantable within the human body and which will respond to the changing needs of the body but will not compete with the natural cardiac electrical activity of any kind.

2. State of the Prior Art

The implantable cardiac pacemaker, shown in U.S. Pat. No. 3,057,356 permits innocuous, painless, long-term cardiac stimulation at low power levels by utilizing a small, completely implanted transistorized and battery-operated pacemaker connected via flexible electrode wires directly to the cardiac muscle. Such an asynchronous pacemaker or pacer, while providing fixed-rate stimulation not automatically changed in accordance with the body's needs, has proven effective in alleviating the symptoms of complete heart block. An asynchronous pacer, however, has the possible disadvantage of competing with the natural, physiological cardiac pacemaker during episodes of normal sinus conduction.

A synchronous or P-wave pacer, shown in U.S. Pat. No. 3,253,596, has been proposed for producing a stimulus following each P-wave or atrial beat. When the body signals a need for increased heart rate, as indicated by an increasing atrial beat, the synchronous pacer responds with an increased ventricular stimulation rate. However, the function of the known synchronous pacer is not responsive to irregular ventricular ectopic activity and may compete against such beats. Thus, while the synchronous pacer will not compete against normally conducted beats, it can compete against ectopic or abnormally conducted beats. Any competition between the natural and the artificial pacer may be undesirable because such competition may possibly lead to incidents of tachycardia or even fibrillation.

There has also been developed a ventricular inhibited or demand-type pacer, shown in U.S. Pat. No. 3,478,746, in which case the artificial stimuli are initiated only when required and subsequently can be eliminated when the heart returns to sinus rhythm above a predetermined base rate. The demand pacer solves the problem arising in asynchronous pacer by inhibiting itself in the presence of ventricular activity but coming "on line" and filling in missed heart beats in the absence of ventricular activity after a base time interval. When the demand pacer comes "on line", it operates as an asynchronous pacer, the rate of which is not responsive to atrial activity.

To cope with the problems of the synchronous pacer, a further pacer has been developed, shown in U.S. Pat. No. 3,648,707, which stimulates the heart asynchronously in the absence of cardiac electrical activity of any kind, inhibits itself and becomes completely dormant for a suitable interval in the presence of a single ventricular beat, ectopic or conducted from the atrium, and stimulates the heart synchronously in the presence of atrial activity not accompanied by arrythmic ventricular activity.

To the best of my knowledge, all versions of the atrial synchronous pacer that have been publicly disclosed and/or marketed have stimulated the heart synchronously in the presence of sensed atrial activity in a certain range extending from the asynchronous lower rate of the pacer circuit up to a maximum upper rate. Any natural P-wave rate exceeding the upper rate results in a sudden change of patient's heart beat and a concurrent sudden loss of cardiac output. Presumably, the patient's atrial rate had risen to the upper limit due to exertion or stress requiring increased cardiac output, and the sudden change in cardiac output could cause that patient to suddenly become faint and possibly be endangered in view of the circumstances causing the atrial rate to rise.

This particular trait of the synchronous pacer was deliberately designed in because a physiological condition of the cardiac muscle left it vulnerable to irritation by external electrical stimulae during a predetermined time period following a complete depolarization of the heart muscle. For example, if the depolarization of the heart is caused by a pacer pulse stimulus synchronously following a sensed atrial depolarization, the heart muscle must repolarize over a predetermined time interval, named the T-wave interval. If a second atrial depolarization is sensed too soon following the first depolarization, the pacer stimulus, if applied to the heart during the vulnerable period might conceivably elicit bursts of tachycardia of fibrillation which are undesirable and may even lead to a fatal sequence of arrythmias.

With this fear in mind, advantage was taken of the fact that sense amplifier circuits in synchronous and demand pacer circuits have a built-in refractory period in which they are insensitive to any incoming signal following too closely a previously sensed signal in order to prevent their sensing the pacer's own stimulus. This refractory period of the sense amplifiers in synchronous pacers was allowed to establish the maximum allowable rate at which the pacer would synchronously follow the atrial depolarizations. As described in U.S. Pat. No. 3,648,707 the refractory period of the atrial sense amplifier might be set at 500 milliseconds, (conforming to a maximum synchronous rate of 120 beats per minute), so that if the atrial depolarizations followed each other by less than 500 milliseconds, and a second P-wave signal would arrive at the P-wave sense amplifier while it was still refractory, only every other atrial depolarization would be sensed and the pacer rate would be one-half the atrial rate. Through the same mechanism, if the atrial rate increases even more, and the atrial depolarization occur within 500 milliseconds, only one would be sensed, and the pacer would operate at one-third the atrial rate.

Alternatively, pacer circuits have been designed to revert to an asynchronous base rate mode once the atrial depolarizations occur at a rate exceeding the upper limit. The asynchronous mode rate is the lower limit at which the pacer circuit functions in the absence of any heart activity. In this case circuit designers have again taken advantage of a pre-existing pacer circuit to effect this operation.

As mentioned earlier, the sudden transition from a high pacing rate to a lower rate, while physiologically beneficial in the sense that cardiac stimulation during the vulnerable period is prevented, causes sudden symptomatic interruption in cardiac output and that may indirectly cause physical harm to the patient.

SUMMARY OF THE INVENTION

Accordingly in recognition of the above-stated disadvantages of the prior art synchronous pacemaker, the present invention provides an artificial cardiac pacemaker which in response to atrial electrical activity, not accompanied by natural ventricular activity, provides ventricular stimulating impulses suitably delayed and in synchronism with the atrial activity, and when the atrial activity exceeds an upper limit for artificial stimulation, the pacer continues to provide ventricular stimulating impulses at a rate approaching the upper limit. The pacer provides the ventricular stimulating impulses in partial synchronism with the atrial activity. In addition, a method of operating such a pacemekaer is contemplated.

In a preferred embodiment of my invention, the artificial cardiac pacer provides stimulating electrical pulses to the heart at a predetermined rate in the absence of natural cardiac electrical activity of any kind. In response to a ventricular beat, either ectopic or conducted and from any source, the pacer inhibits itself and becomes completely dormant for a suitable interval. In response to atrial electrical activity, not accompanied by natural ventricular activity, the pacer provides stimulating pulses suitably delayed and in synchronism with the atrial beats.

Advantageously to the patient, the artificial cardiac pacer of my invention does not suddenly revert to a lower stimulating rate when atrial activity exceeds an upper limit, thus lowering cardiac output when the patient may need it the most.

The foregoing and additional advantages and characterizing features of the present invention will become clearly apparent upon reading of the ensuing detailed description of an illustrative embodiment thereof together with the included drawings depicting the same.

BRIEF DESCRIPTION OF THE DRAWINGS

FIG. 2 is a block diagram illustrating a preferred embodiment of an artificial pacer according to the present invention;

DETAILED DESCRIPTION OF THE ILLUSTRATED EMBODIMENT

Figure 1:
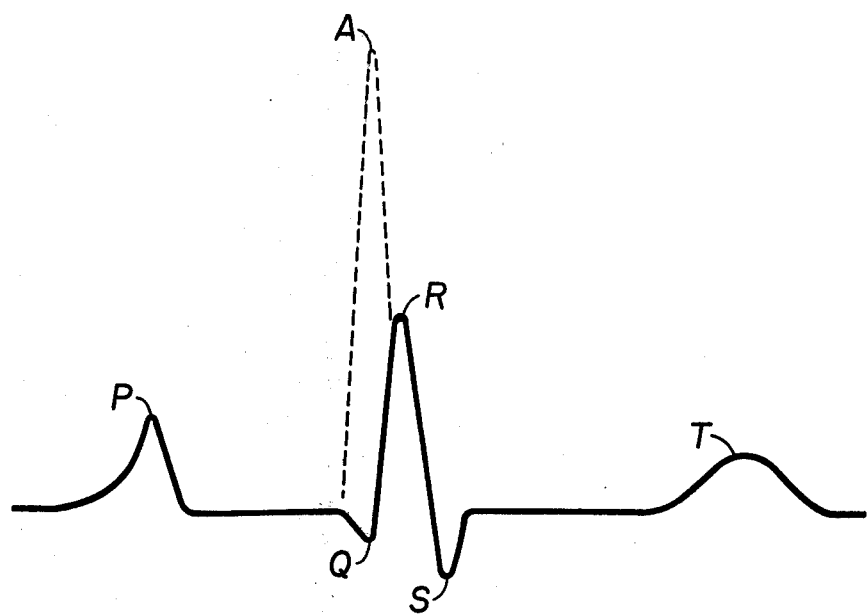
FIG. 1 illustrates the voltage wave produced by an animal heart during one complete heart beat.

The human heart beat is represented electrically as a complex wave consisting of what are designated "P," "Q," "R," "S" and "T" waves all as shown in FIG. 1. The P-wave electrically represents an atrial beat associated with atrial depolarization which beat commands heart rate as a function of signals from the rest of the body depicting the required cardiac output. The major and most pronounced electrical pulse in the heart is the R-wave and is normally of a magnitude between 2 to 20 millivolts in the ventricle. The R-wave, which stimulates and represents ventricular contraction, typically has an amplitude relation to the P-wave of at least three to one. The R-wave normally is generated by depolarization of the ventricles, but when not so produced due to some cardiac malfunction, it is the function of the artificial pacer to provide periodic electronic pulses to the heart to supply a missing R-wave. If both the natural and artificial pacer supply an R-wave, however, competition for control of the heart results and a possibly dangerous situation arises when the pacer electronic pulse occurs in a T-wave region. The T-wave portion of each complete heart beat follows the R-wave or major beat pulse thereof by about 0.3 seconds. Within the T-wave is a critical interval known as the "vulnerable period" and, in the case of a highly abnormal heart, a pacer impulse falling into this period can conceivably elicit bursts of trachycardia or fibrillation which are undesirably and may even lead to fatal sequence of arrythmias.

The waves depicted in FIG. 1 may be picked up and recorded or displayed by electrocardiogram apparatus. When an electrocardiogram records or displays an artificial cardiac pacer impulse, that impulse may be referred to as a pacer artifact or spike. Thus in the drawings, the artifact is designated "A".

FIG. 2 shows in block diagram form an artificial cardiac pacer constructed in accordance with the present invention. The pacer includes pulse generating means 10 for providing stimulating pulses to the heart under certain conditions and at a preset rate controlled by oscillator timing means 12 included therein. A first electrode 14 is coupled to pulse generating means 10 and is adapted to be operatively connected to a patient's heart on or in the ventricle thereof. An indifferent electrode 16, which functions as a reference or indifferent electrode, can be placed in contact with another portion of the patient's body or even with a selected portion of the patient's heart. A disc shape is shown for the indifferent electrode 16, since indifferent electrodes for pacers often comprise conductive discs or shields on the surface of the implanted pulse generator. The pacer includes a second electrode 18 adapted to be operatively connected to a patient's heart on or in the atrium thereof. The artial electrode 18 is coupled to another component of the pacer as will be described presently.

The electrode arrangement shown is preferred, although others can be substituted without departing from the spirit and scope of the present invention. Only one ventricular electrode 14 is needed and is placed surgically on or in the ventricle of the heart. The indifferent electrode 16 can be subcutaneously implanted. At least electrode 14 is of the type which provides a sensing function as well as a stimulating function, although a separate electrode structure for sensing ventricular electrical signals can be provided. Electrode 18 is placed surgically on or in the atrium of a patient's heart.

Indifferent electrode 16 is coupled through a lead 20 and a ground bus 22 connected thereto to pulse generating means 10. Electrode 16 serves an electrical ground for pulse generating means 10 and also as a ground for other circuit components of the pacer as will be described presently.

The pacer provided by the present invention also comprises a first signal responsive mean 24 which is responsive to ventricular electrical signals in the heart and thus also may be called an R-wave detector. First signal responsive means 24 is coupled to ventricular electrode 14 through leads 26 and 28. Ventricular electrode 14 is also coupled to the output of pulse generator 10 through leads 26 and 30. Signal responsive means or R-wave detector 24 is operatively connected through a lead 39 to a RESET terminal of pulse generator 10, and a ventricular signal, such as an R-wave, produced in the heart is sensed by means 24, the signal is amplified therein by sense amplifier 25, and pulse generator 10 is reset or recycled so that no stimulating pulse will be sent to the heart by the pacemaker. The sense amplifier 25 of R-wave detector 24 is rendered insensitive to any input signal on lead 28 for a period of time, characterized as the refractory period, established by a refractory circuit 34. In this case, the refractory period is chosen to be 300 milliseconds (ms). The refractory circuit 34 is rendered operative to inhibit the sense amplifier 25 by an amplified R-wave received through diode 37 and leads 36 and 38 or by an oscillator output signal received from oscillator 12 on lead 40 and through diode 42. A detailed description of the circuitry and operation of the R-wave detector 24 will be presented further on in the specification.

Pulse generator means 10 comprises an oscillator 12 which, in the absence of an amplified R-wave signal at its RESET input or an output of the upper rate memory circuit 44 at its TRIGGER input (the operation of which will be described in due course) freely oscillates at a preset rate of, for example, 60 beats per minute (a pulse interval of 1000 ms). The 60 beats per minute established by the oscillator 12 constitutes the lower pacing rate of the pacer. The oscillator output signal developed by the oscillator 12 is conducted by a lead 46 to a pulse amplifier 48 which amplifies the output signal to a voltage and current sufficient to stimulate the patient's ventricles, and that pacemaker stimulus is applied to the ventricular electrode 14 through leads 30 and 26. The pacemaker stimulus or artifact is designated "A" in the drawings. The oscillator 12 has an upper limit above which it is inhibited from either freely oscillating in case of a circuit or battery malfunction or being driven by the second signal responsive means 48 (in a manner to be described). That upper limit is established by a rate limit circuit 50 which is rendered operative to inhibit the oscillator 12 for a predetermined period following the receipt of an oscillator output signal through leads 46, 40 and 52. The upper limit, for example, may be 120 beats per minute which conforms to a time interval between oscillator output signals of 500 ms.

The second signal responsive means 48 is responsive to natural atrial beats of the heart picked up by the atrial electrode 18 and conducted to a sense amplifier 54 by lead 56 and may be designated a P-wave detector. The sense ampifier 54 is also rendered refractory or insensitive for a refractory period (150 ms, for example) established by a refractory circuit 58. Refractory circuit 58, through diodes 37 and 60 and leads 36, 39, 40, 62 and 64, is rendered operative whenever the R-wave detector 24 amplifies an R-wave to prevent the P-wave detector 48 from also responding to the same R-wave if it is subsequently picked up by the atrial electrode 18 after traveling from the ventricle to the atrium. Refractory circuit 58 through diodes 42 and 60 and leads 40, 61, 62 and 64 also renders sense amplifier 54 refractory to oscillator output signals developed by the pulse generator 10, and associated cardiac signals for 150 ms. Finally, refractory circuit 58, through leads 62 and 64, also renders sense amplifier 54 refractory for 150 ms following the sense amplifier's own detection and amplification of a P-wave signal.

The output of P-wave detector 48 is coupled to an upper rate memory circuit 44 which in the normal course of operation of the pacer (i.e., below the upper limit in a P-wave synchronous mode) introduces a P-R delay of about 100 ms between the detection of a P-wave and the production of a pacer impulse A by the pulse generator 10. The upper rate memory circuit 44 comprises a memory 66 that can be "Set" by the amplified P-wave conducted on lead 62 to its "Set" input and can be "Cleared" by either an amplified R-wave signal developed by R-wave detector 24 (diode 37 and leads 36, 39 and 40) or by an oscillator output signal developed by oscillator 12 (through leads 40 and 61 and diodes 42 and 60) that are each simultaneously applied to both the Set and Clear inputs of memory 66.

Whenever the memory 66 is set by an amplified P-wave signal at its Set input, it generates a memory output signal on lead 68. Whenever the memory 66 is Cleared by either an amplified R-wave signal or the oscillator output signal, memory 66 is cleared and the memory output signal is removed from lead 68. The memory 66 may be a bistable multivibrator or flip-flop of any conventional design, having bistable states of operation.

The memory output signal is conducted by lead 68 to a P-R interval time delay circuit 70. The circuit 70 may be of any conventional time delay circuit design having the capability of responding to a memory output signal and that has a preset interval of from 80 to 150 ms, which interval is chosen to correspond to the average interval between the naturally occurring P-wave and the subsequent R-wave of a normal heart beating within a normal range. Preferably, the P-R interval is set to 100 ms. The circuit 70 will not respond to a memory output signal that does not last at least as long as the preset inverval, for reasons to be explained.

The P-R time delay circuit 70 responds to the memory signal to produce a TRIGGER signal that is conducted by lead 72 to the TRIGGER input of the oscillator 12. The oscillator 12 responds by immediately producing the oscillator output signal on lead 46, which is amplified and applied to the patient's ventricle. The oscillator output signal also, as mentioned earlier, resets the oscillator 12, clears memory 66 and renders the R-wave and P-wave detectors refractory. Thus, the total time interval from the detection of the P-wave until the stimulation of the ventricle is approximately 80 to 150 ms, and the pacer circuit is nonresponsive to any subsequent R-wave signal for at least 300 ms.

Figure 3:
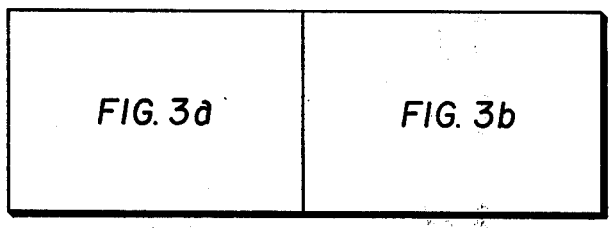
FIG. 3 is a block diagram of the relationship of FIGS. 3a and 3b.
Figure 3A:
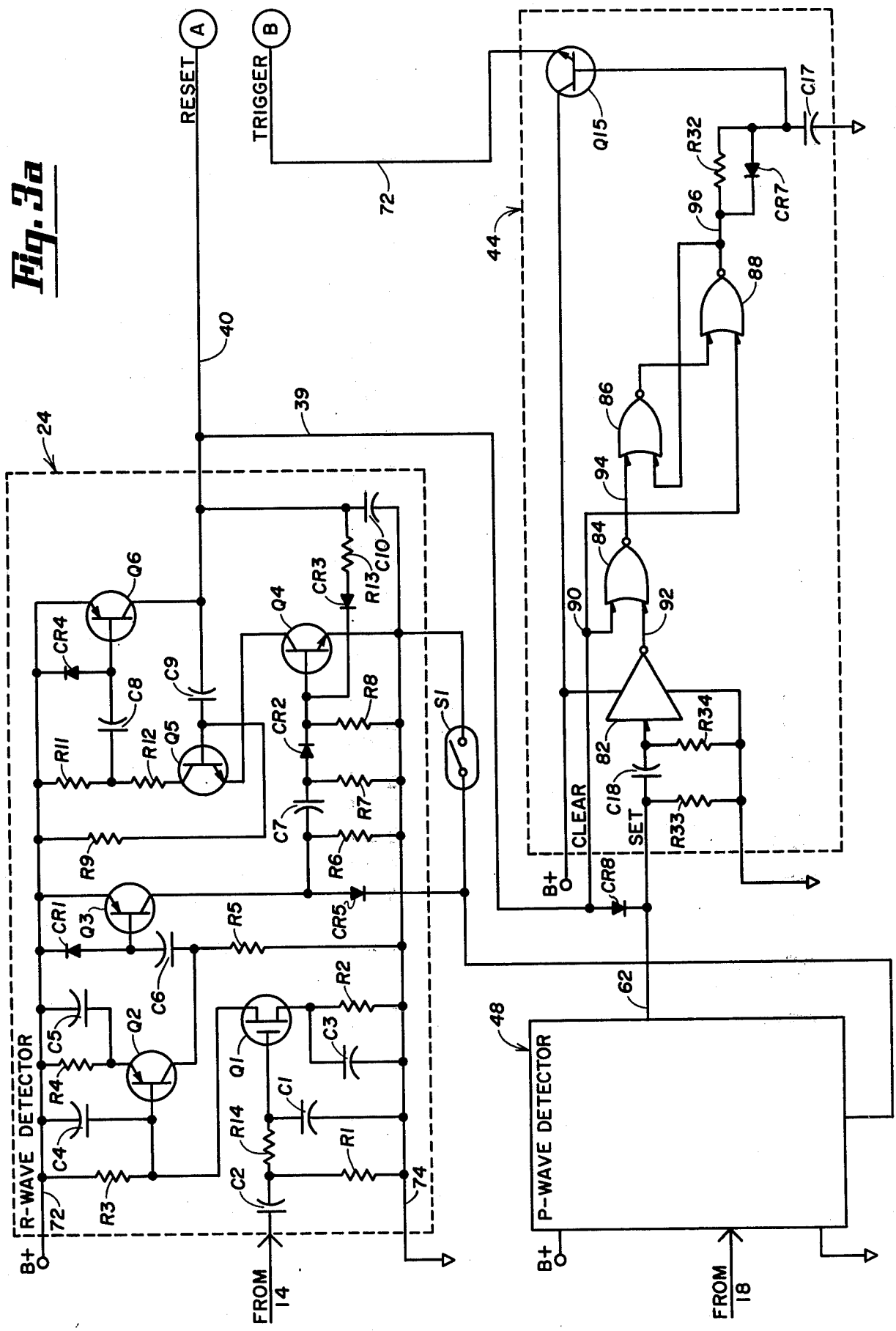
FIGS. 3a and 3b are schematic diagrams of the circuitry included in the block diagram of FIG. 2.
Figure 3B:
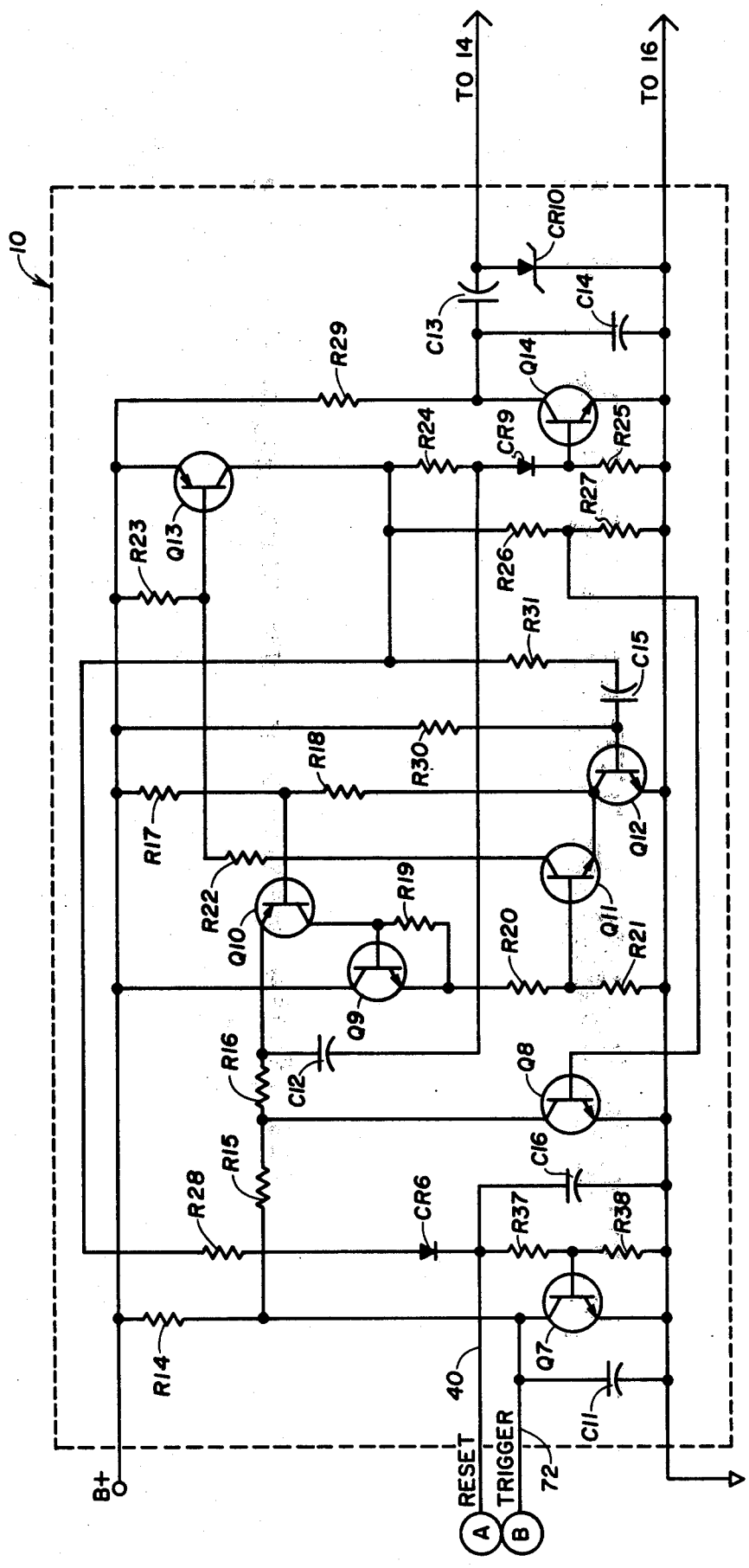

Referring now to FIGS. 3a and 3b considered side-by-side in the manner depicted in FIG. 3, there is shown a schematic of a complete diagram of an illustrative embodiment of an artificial cardiac pacemaker pulse generator circuit operable as described above with respect to FIG. 2. The circuits 10, 24, 44 and 48 and the interconnecting leads may be enclosed or hermetically sealed within an electromagnetic interference shield, which, in this illustrative embodiment, may form the circuit's indifferent electrode 16. Each of the circuits 10, 24, 44 and 48 are energized by a common power source comprising a plurality of batteries B+ (not shown) serially coupled in parallel across a capacitor (not shown) and each of the circuits.

The R-wave and P-wave detector circuits, 24 and 48, are identical except for time constants of the refractory portions of the circuit, that will be further explained. Consequently, only the particular circuitry of the R-wave detector 24 is depicted and described.

In FIG. 3a, the R-wave is applied through a filter circuit comprised of capacitors C1 and C2 and resistors R1 and R14 to the gate electrode of an FET Q1. The amplified output of FET Q1 is in turn applied to the base of transistor Q2 for a second stage of amplification. Capacitor C6, connected in series with resistor R5 and diode CR1 across positive and ground buses 72 and 74, is normally charged. When transistor Q2 is rendered more or less conductive by the greater conduction or lower conduction of FET Q1, the voltage on capacitor C6 changes accordingly. If the sensed amplitude of the R-wave is above a predetermined level, e.g., ± 3mV, the charge on capacitor C6 is altered to a voltage sufficient to turn normally non-conducting transistor Q3 on. The sensing and amplifying circuit of FIG. 3a is responsive to positive and negative R-wave signals. In particular, if a heart signal of a polarity is present to produce a negative potential upon the collector of transistor Q2, a current will be drawn through the emitter-to-base path of transistor Q3 and capacitor C6, whereby transistor Q3 is turned on. On the other hand, if a heart signal of an opposite polarity is placed upon the input of the sensing and amplifying circuit, a positive potential appears upon the collector of transistor Q2, thereby tending to turn transistor Q3 off. However, when the positive potential is removed from the collector of transistor Q2, capacitor C6 (discharged through diode CR1) charges through the base-emitter junction of transistor Q3 whereby transistor Q3 is turned on at that time.

A magnetically-actuated switch S1 is connected through diode CR5 between the collector of transistor Q3 and the ground bus 74. Similarly, the switch S1 is connected to the same point in the P-wave detector circuit 48, and it serves to disable both of the sense amplifier circuits when it is magnetically closed. The switch S1 is inserted into the circuit to permit the doctor to disable the sensing and amplifying circuit by actuating the switch S1 with a suitable magnetic field and thereby clamping the collector of transistor Q3 to the forward voltage of diode CR5. With the sense amplifier circuits defeated, the oscillator circuit 12 (FIG. 2) will freely oscillate and produce stimulating signals at a rate dependent on the battery voltage. Thus, the doctor may determine the operability of the pulse generator and the state of its batteries by monitoring the free-running rate and comparing the presently measured rate to the rate it exhibited at the time of implant.

Further, the collector of transistor Q3 is coupled in turn by a capacitor C7 and diode CR2 to the base of transistor Q4. If the amplitude of the heart signal is above the predetermined level, the transistor Q3 is rendered conductive, thereby raising the voltage applied through the capacitor C7 to the base of transistor Q4 toward the B+ potential, thereby turning transistor Q4 on. In this manner, the heart signal is amplified and sensed, and if it is above the predetermined level, transistor Q4 is rendered capable of conducting.

When normally non-conductive transistor Q4 is rendered capable of conducting, transistor Q5, which has its emitter-collector current conduction path in series with the emitter-collector current conduction path of transistor Q4 and resistors R11 and R12 across the B+ source, is also rendered conductive since forward bias as applied to its base by resistor R9. When transistors Q4 and Q5 conduct, the voltage at the junction of resistors R11 and R12 abruptly decreases tending to make capacitor C8 charge to the voltage drop across resistor R11. Charging current for capacitor C8 is drawn from B+ through the emitter-base junction of transistor Q6 which tends to render it conductive. Capacitor C8 can charge to the voltage drop across resistor R11 less the emitter-base forward voltage drop of transistor Q6.

Although the amplified R-wave signal at the base of transistor Q4 is of relatively short duration, while transistors Q4, Q5 and Q6 are rendered conductive, voltage through transistor Q6, resistor R13 and diode CR13 tends to maintain transistor Q4 in conduction. Therefore, as long as capacitor C8 charges and transistor Q6 remains conductive, transistors Q4 and Q5 are also maintained conductive. The conduction of transistor Q6 tends to charge capacitor C9 which is coupled to the base of transistor Q5 to battery voltage. While capacitor C9 charges, transistor Q5 remains conductive. However, when capacitor C8 is fully charged, transistor Q6 turns off and capacitor C9 begins to discharge. The charge time of capacitor C8 establishes the relatively short pulse width of the amplified R-wave signal on lead 39. While capacitor C9 discharges the base voltage on transistor Q5 is lowered to a level insufficient to allow it to conduct, thus turning it off. The discharge time of capacitor C9 is selected to be about 300 ms, and during that time the circuit is incapable of responding to an incoming R-wave signal. When transistor Q5 is turned off, the capacitor C8 becomes reverse biased and transistor Q6 is further turned off and capacitor C8 discharges. Thus although transistor Q6 is conductive only a short period of time, to produce the signal b) on conductor 39, the circuit is refractory for a period of time dependent on the value of capacitors C9, C10 and R9.

It will be noted in FIG. 3a that the refractory circuit 34 is integral with the sense amplifier circuit 25, the two circuits sharing lead 40 for the transmission of outgoing amplified R-wave signals and the receipt of incoming oscillator reset signals. An incoming oscillator reset signal is conducted by resistor R13 and diode CR3 to the base of transistor Q4, rendering transistor Q4 conductive in the manner hereinbefore described. Again in this case, transistors Q5 and Q6 are rendered conductive. Capacitor C9 is charged and re-establishes the refractory period as it discharges. Capacitor C10 is a relatively small capacitor and it acts as a filter to prevent high frequency noise from triggering transistor Q4 into conduction.

Turning now to the pulse generator 10, (FIG. 3b) it includes oscillator 12 comprising the circuitry associated with transistors Q7, Q8, Q9 and Q10, the rate limit circuit 50 comprising the circuitry associated with transistor Q12, and the pulse amplifier circuit 48 comprising the circuitry associated with transistors Q11, Q13 and Q14.

Referring first to the oscillator portion, in the absence of the normal operation of the patient's heart as indicated by the amplified R-wave or P-wave signal, a timing capacitor C11 is charged by current through the timing resistor R14 at a rare determined by the R-C time constant of the series time constant means; the rate of charging capacitor C11 to a reference voltage level determines the base rate at which stimulating pulses are to be applied by the artificial cardiac pacemaker to the patient's ventricle. The voltage charge developed on capacitor C11 is applied through resistors R15 and R16 to the emitter of transistor Q10, and upon reaching a predetermined level in excess of the reference voltage established upon its base at the junction of resistors R17 and R18, transistor Q10 is rendered conductive. In turn, transistor Q10, upon being rendered conductive, raises the voltage applied to the base of transistor Q9 whereby it is also turned on. As seen in FIG. 3b, the collector of transistor Q10 is coupled directly to the base of transistor Q9 and upon being rendered conductive, raises the voltage applied thereto, turning transistor Q9 on. When transistor Q9 is rendered conductive, potential is applied through resistors R20 and R21 to the base of the first output transistor Q11, thereby turning it on for a pulse width period determined in a manner to be explained.

The conduction of transistors Q9 and Q10 of the oscillator circuit and the subsequent conduction of the first output transistor Q11 is conditioned on the fact that the rate limit transistor Q12 is also conductive, for the emitter-collector path of transistor Q12 is in series with the reference voltage divider circuit of resistors R17 and R18. For the time being, the "on" or conducting state of transistor Q12 is presumed.

The emitter-collector path of the first output transistor Q11 is also connected in series with the emitter-collector path of transistor Q12 and with resistors R22 and R23. With positive voltage applied to its base on the conduction of transistors Q9 and Q10, transistor Q11 is turned on to lower the voltage at the junction of resistors R22 and R23, which junction is coupled to the base of second output transistor Q13. The emitter-collector path of second output transistor Q13 is connected in series with resistor 24, diode CR9 and resistor R25 and transistor Q13 is rendered conductive by the lower voltage on its base.

As the voltage at the collector of transistor Q13 is raised, a correspondingly more positive voltage is applied through resistor R28, diode CR6 (42 of FIG. 2) and the resistors R37 and R38 to the base of reset transistor Q7, whereby it is rendered conductive, thereby discharging timing capacitor C11 through its collector-emitter path in preparation for the next cycle of operation of the R-C timing circuit comprising R14 and C11. The reset signal is also conducted through diode CR6 and leads 40 and 39 to the refractory circuit of the R-wave detector 24 and the Clear input of the memory 66, and through additional diode 60 to the refractory circuit of the P-wave detector 48 and the Set input of the memory 66.

Departing for a moment from the further explanation of the pulse generator 10, the response of detector circuits 24 and 48 to the reset signal from the pulse generator will be explained. As explained earlier the mechanism by which the sense amplifiers are rendered refractory centers on the sustained low voltage on the base of transistor Q5. Without repeating the full operation of transistors Q4, Q5 and Q6, let it suffice to say that for the time period while capacitor C9 discharges from battery voltage to a voltage level insufficient to reverse bias transistor Q5, any sensed signal on the base of transistor Q4 will fail to render it conductive and produce an amplified R-wave signal on lead 39. The same explanation would apply to the circuitry of the P-wave detector.

Referring back to the pulse generator circuit 10, the conduction of transistor Q13 allows battery current to flow through resistor R24, diode CR9 and resistor R25 and the voltage across resistor R25 is conducted to the base of the power output transistor Q14 that is rendered conductive thereby. The conduction of transistor Q14 precipitates the rapid discharge of voltage on output capacitor C13 through ventricular electrode 14, the patient's heart and back through the indifferent electrode 16. The condenser C13 recharges in the interval between the pacemaker output pulses from the battery source B+ through resistor R29 and the aforementioned electrodes. Capacitor C13 discharges rapidly and the amplitude and pulse width of the pacemaker output signal is selected to exceed the heart's stimulation threshold. However, capacitor C13 recharges slowly due to the high resistance of resistor R29, and the recharge current is held below the heart's stimulation threshold.

The condensor C14 and the zener diode CR10 protect the pacemaker circuitry from any large amplitude electrical signals picked up by electrode 14 from external sources.

Referring to the pulse width of the pacer output pulses or artifacts, pulse with controlling circuitry transistor Q8 and capacitor C12 are provided. When transistors Q9 and Q10 are non-conductive, capacitor C12 tends to charge with capacitor C11 through the series circuit including resistors R14, R15, R16, capacitor C12, divide CR5 and diode CR9. The voltage on capacitor C12 will follow the voltage on capacitor C11.

When transistor Q13 conducts, however, a voltage is developed across the voltage divider circuit in series therewith comprising resistors R26 and R27. The junction of resistors R26 and R27 is connected to the base of normally non-conductive, pulse width extending transistor Q8, the emitter-collector path of which is connected between the junction of resistors R15 and R16. Transistor Q8 is rendered conductive by the voltage on resistor R27 developed when transistor Q13 is conductive so long as the voltage on power source battery B+ normal. The voltage on capacitor C12 discharges through resistor R16, and reset transistor Q8 in that case. At the same time, current conducted through transistor Q13 and resistor R24 is applied to the opposite plate of the capacitor C12 tending to charge capacitor C12 in the opposite direction.

When transistors Q7 and Q8 are rendered conductive, voltage on the emitter of transistor Q10 drops towards ground potential, and tends to render transistor Q10 non-conductive. However, the charging voltage from transistor Q13 through resistor R24 and capacitor C12 tends to maintain transistor Q10 in conduction for an interval dependent on its rate of charge of capacitor 12. By careful selection of the values of the resistors mentioned above and resistor R16 and capacitor C12, this interval which controls the interval during which transistor Q14 is conductive, and consequently the pulse width of the pacer output pulse, can be preset. By the addition of a remotely variable resistance in the circuit, the pulse width may be changed as found physiologically beneficial to the patient. A typical pulse width of the stimulator pulse, ranges from 0.5 to 1.2 ms, whereupon the transistor Q10 is turned off. As a result, transistors Q9, Q11, Q13 and Q14 are turned off to terminate the pulse output of the pacemaker circuit 10 as derived from the transistor Q14. As transistor Q13 is rendered nonconductive the reset pulse on the base of transistor Q7 terminates, thus permitting capacitor C11 to recharge to initiate the next cycle of operation in a manner as explained above. Further, capacitor C12 begins to recharge when transistors Q7 and Q8 are rendered non-conductive. The pulse width of the pacemaker artifact is automatically widened, when the battery source voltage B+ drops due to its depletion, to insure that the pacemaker stimulus has sufficient energy to retain capture, i.e., depolarize, the heart muscle. The pulse width extending transistor Q8 accomplishes this by failing to conduct, due to a lower voltage at its base and across resistor R27, whereupon the capacitor C12 must discharge through the additional resistor R15 and reset transistor Q7. The additional resistor in the circuit extends the discharge time and the "on" time of transistor Q10 to increase the pacemaker stimulus pulse width.

Thus, as the pulse generator circuit 10 has been described heretofore, it operates in an inhibited mode designated Mode I and a demand mode designated Mode II upon the timely receipt of a reset signal that renders transistor Q7 conductive to discharge capacitor C11 and reset the timing interval, and in an asynchronous mode designated Mode III when the R-C timing circuit is allowed to fully time out whereupon the oscillator circuit resets itself. The operation of the circuit of FIG.'s 2 and 3 in the remaining synchronous modes designated Modes IV and V requires an explanation of the rate limit circuit of the pulse generator 10 and the upper rate memory circuit 44 to follow.

In FIG. 3b, the pulse generator circuit includes the aforementioned normally conductive rate limit transistor Q12 whose collector is connected to the base of transistor Q10 through resistor R18 and whose emitter is connected to the ground bus 74. The base of rate limit transistor Q12 is connected through resistor R30 to the battery voltage and also through capacitor C15 and resistor R31 to the collector of normally non-conductive second output transistor Q13. The transistor Q12 serves in prior art oscillator circuits to prevent the oscillator circuit from stimulating the patient's heart at too fast a rate in the event one of the oscillator timing elements should become defective in any manner. For example, if the resistance R17 becomes an open circuit, the transistor Q10 would turn on prematurely with the result that a very rapid, possibly dangerous series of stimulating pulses would be applied to the patients's heart. In operation, transistor Q12 is normally biased to a conducting state by the battery voltage through resistor R30. To terminate the pulse width of the artificial stimulus, transistor Q10 is rendered non-conductive in a manner as explained above, whereby transistors Q9, Q11 and Q13 are also rendered non-conductive. However, while transistor Q13 has been conductive, capacitor C15 connected to the base of transistor Q12 charges. When transistor Q13 is turned off, the negative charge established upon capacitor C15 serves to bias off transistor Q12, thereby preventing transistor Q12 from being turned on again for a period dependent upon the discharge time of capacitor C15. As shown in FIG. 3b, capacitor C15 discharges primarily through resistors R30, R31, R26, R27, R24, diode CR9 and R25, the discharge time being in the order of 500 ms. While transistor Q12 is rendered non-conductive, transistor Q10 and therefore transistors Q9, Q11, Q13 and Q14 may not be turned on. Thus, if one of the elements within the oscillator circuit becomes defective, thereby tending to turn transistor Q10 on prematurely, transistor Q12 serves a protective function, preventing the premature conduction of the noted transistors and therefore limits the rate at which stimulating pulses may be applied to the patient's heart, to a rate in the order of 120 beats per minute.

The rate limit circuit therefore, inhibits pacemaker runaway in Modes I through III. In this preferred embodiment of my invention, advantage is also taken of its action in the P-wave synchronous mode of Modes IV and V. In short, in the synchronous mode, amplified P-wave signals that Set the memory circuit of the upper rate memory circuit 44 produce a trigger signal that is applied directly across the timing capacitor C11 and very rapidly increases the voltage thereon to that necessary to render transistor Q10 conductive and produce a ventricular stimulation pulse in the manner explained above. However, if the rate limit has not yet timed out, the pulse signal will be ineffective until the rate limit circuit does time out. Consequently, the pacemaker cannot be driven in synchronism with the heart's P-waves at a rate exceeding 120 beats per minute.

Turning now to the upper memory circuit 44 in FIG. 3a, it comprises a memory circuit (66 in FIG. 2) including the inverter 82, NOR gates 84, 86 and 88, and a time delay circuit (70 in FIG. 2) including resistor R32, diode CR7, capacitor C17 and transistor Q15. Of course, the inverter 82 and NOR gates 84, 86 and 88 may also comprise solid state circuits that are conventional in nature and, for convenience sake, are not reproduced herein. As is well known, an inverter responds to an input signal at its input terminal of either positive or negative polarity, inverts the polarity of that signal and produces the inverted signal at its output terminal. A NOR gate such as gate 84 functions to invert the polarity of and pass or block signals at its two input terminals (90 and 92, for example) as follows:

| 90 | 92 | OUTPUT (94) |
|---|---|---|
| LOW | LOW | HIGH |
| HIGH | LOW | LOW |
| LOW | HIGH | LOW |
| HIGH | HIGH | LOW |

Figure 4:
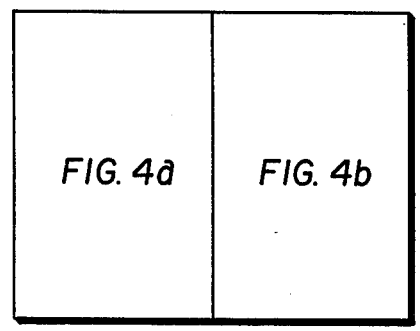
FIG. 4 is a block diagram of the relationship of FIGS. 4a and 4b.

In FIG. 3a, the input terminal 92 is normally HIGH in the absence of a Set signal due to the fact that inverter inverts its normally LOW input voltage. If the presence of a reset signal from the pulse generator 10 or an amplified R-wave from R-wave detector are characterized as HIGH signals on the Clear input (terminal 90) and the presence of any of the aforementioned input signals on the Set input generates a LOW signal from inverter 82 at input terminal 92, the three NOR gates interconnected as shown in FIG. 4 respond as follows:

| 90 | 92 | 96 |
|---|---|---|
| LOW (normal) | HIGH (normal) | LOW |
| HIGH (input) | HIGH (normal) | LOW |
| HIGH (input) | LOW (input) | LOW |
| LOW (normal) | LOW (input) | HIGH |

From the logic table it can be appreciated that the memory output is normally LOW or is rendered LOW in all possible situations except when only an input signal appears on the Set input. The memory is bistable; that is, it remains in a stable HIGH or LOW state ot terminal 96 until a combination of HIGH and LOW signals capable of changing its state next appears at the Set of Clear inputs.

Connected between the Set input and the inverter 82 is a differentiating circuit comprising resistors R33 and R34 and capacitor C18 designed to to assure that a HIGH Clear signal lasts longer than the transient LOW Set signal on input 92.

In the P-R time delay circuit, transistor Q15 is connected in emitter follower relation to battery source bus at its collector, to timing capacitor C11 via lead 72 at its emitter and capacitor C17 at its base. When voltage on its base exceeds that on its emitter, transistor Q15 is rendered conductive to a degree sufficient to raise the voltage on its emitter to that on its base less the base-emitter forward voltage drop of the transistor.

The delay circuit connected between output 96 and lead 72 in its normal quiescent state is non-conductive and does not provide a TRIGGER signal to timing capacitor C11. This is because with a LOW output at 96, capacitor C17 is discharged through diode CR7 and cannot bias transistor Q15 into conduction. The LOW state my correspond to ground potential or a negative voltage that is reflected on the base of transistor Q15. However, when the memory is Set, a HIGH positive voltage at 96 tends to charge capacitor C17 through resistor R32 at a rate dependent on the R-C time constant of resistor R32 and capacitor C17. For example, the values of the HIGH positive voltage, resistor R32 and capacitor C17 may be chosen so that capacitor C17 charges over an interval of 100 ms to the reference voltage on the base of transistor Q10 (FIG. 3b) to forward bias transistor Q15 into conduction (unless the voltage on capacitor C11 has already reached the reference voltage level) as soon as the voltage on capacitor C17 exceeds the voltage then on capacitor C11 plus the base-emitter forward voltage drop. Regardless of the voltage on capacitor C11 at the time during the 100 ms interval that transistor Q15 conducts, capacitor C11 then charges at the R-C time constant of resistor R32 and capacitor C17 so that at the end of 100 ms it has reached the reference voltage (less the emitter-collector voltage drop of transistor Q15).

If the rate limit circuit of the pulse generator 10 has not yet timed out following the 100 ms time delay, capacitor C11 continues to charge to battery voltage and will render transistor Q9 and Q10 conductive when the rate limit interval elapses and rate limit transistor Q12 again conducts. As described hereinbefore, when the rate limit circuit does time out, and transistors Q13 and Q14 are then also rendered conductive, a pacing pulse or stimulus is applied to the ventricular electrode 14, a reset signal is conducted from pulse generator 10 on lead 40 to the Clear input and through diode CR8 to the Set input terminal. The reset signal is simultaneously HIGH at input 90 and LOW (through the action of inverter 82) at input 92 which switches the state of the memory to the LOW state at output 96. The voltage on capacitor C17 rapidly discharges through diode CR7 and output 96 and renders transistor Q15 incapable of conducting. Capacitor C11 is simultaneously discharged.

It should be noted with respect to the above-explained operation of the time delay circuit that if the memory output is reset to the LOW state within 100 ms since it was set to the HIGH state, the capacitor C17 may charge to a level sufficient to bias transistor Q15 into conduction and consequently charge capacitor C11 to a corresponding level. This operation is reflected in the operation of the circuit in accordance with Mode I of FIG. 4a. However, if the memory circuit is Cleared, it means that a reset signal was produced in the circuit and that the reset signal simultaneously is applied to reset transistor Q7, to discharge capacitor C11. In that way, the pulse generator 10 is inhibited from producing a pacemaker stimulus.

Figure 4A:
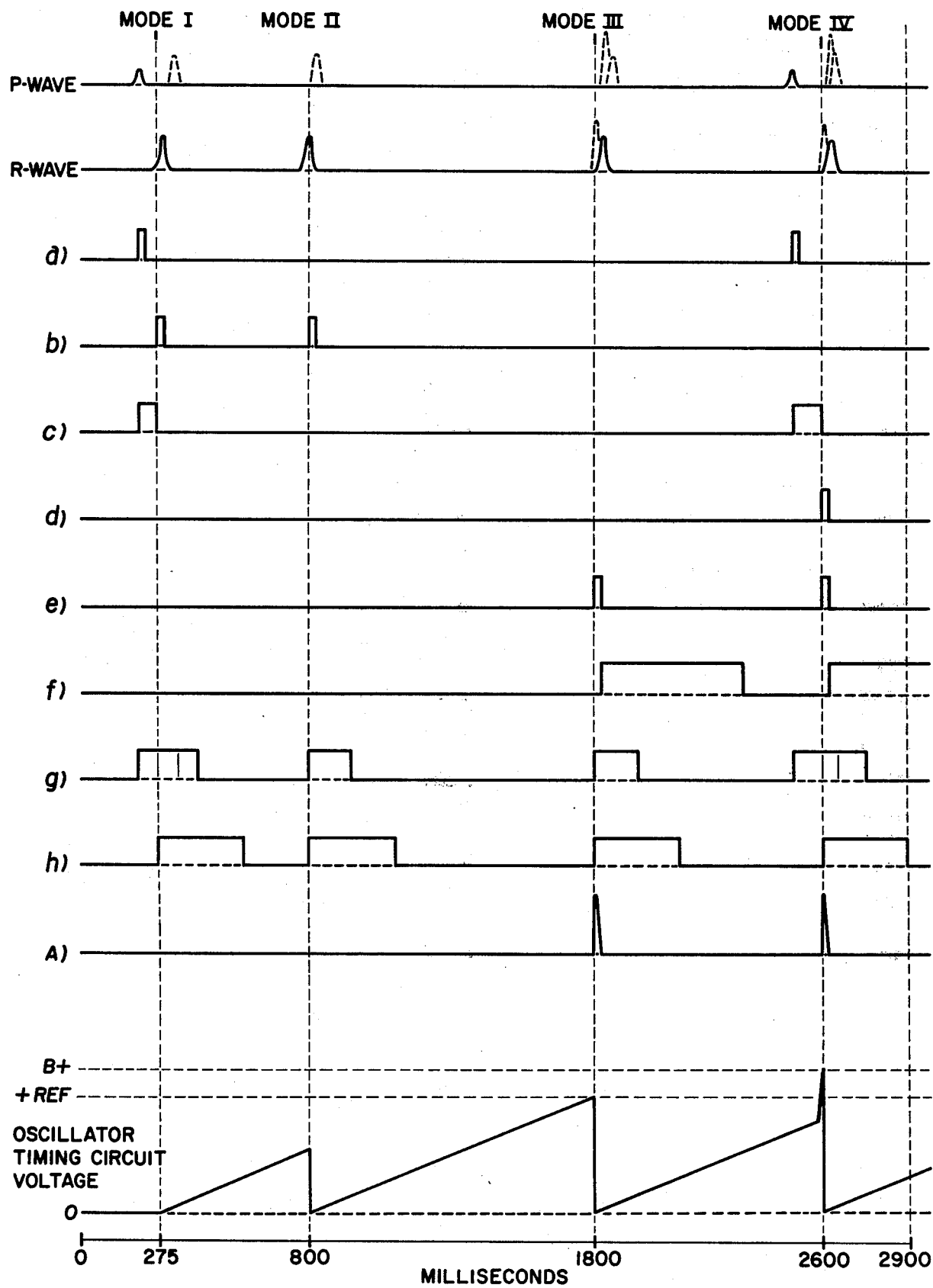
FIGS. 4a and 4b illustrate the signals sensed by or developed at various points in the schematic and block diagrams during several modes of operation of the preferred embodiment of my invention.
Figure 4B:
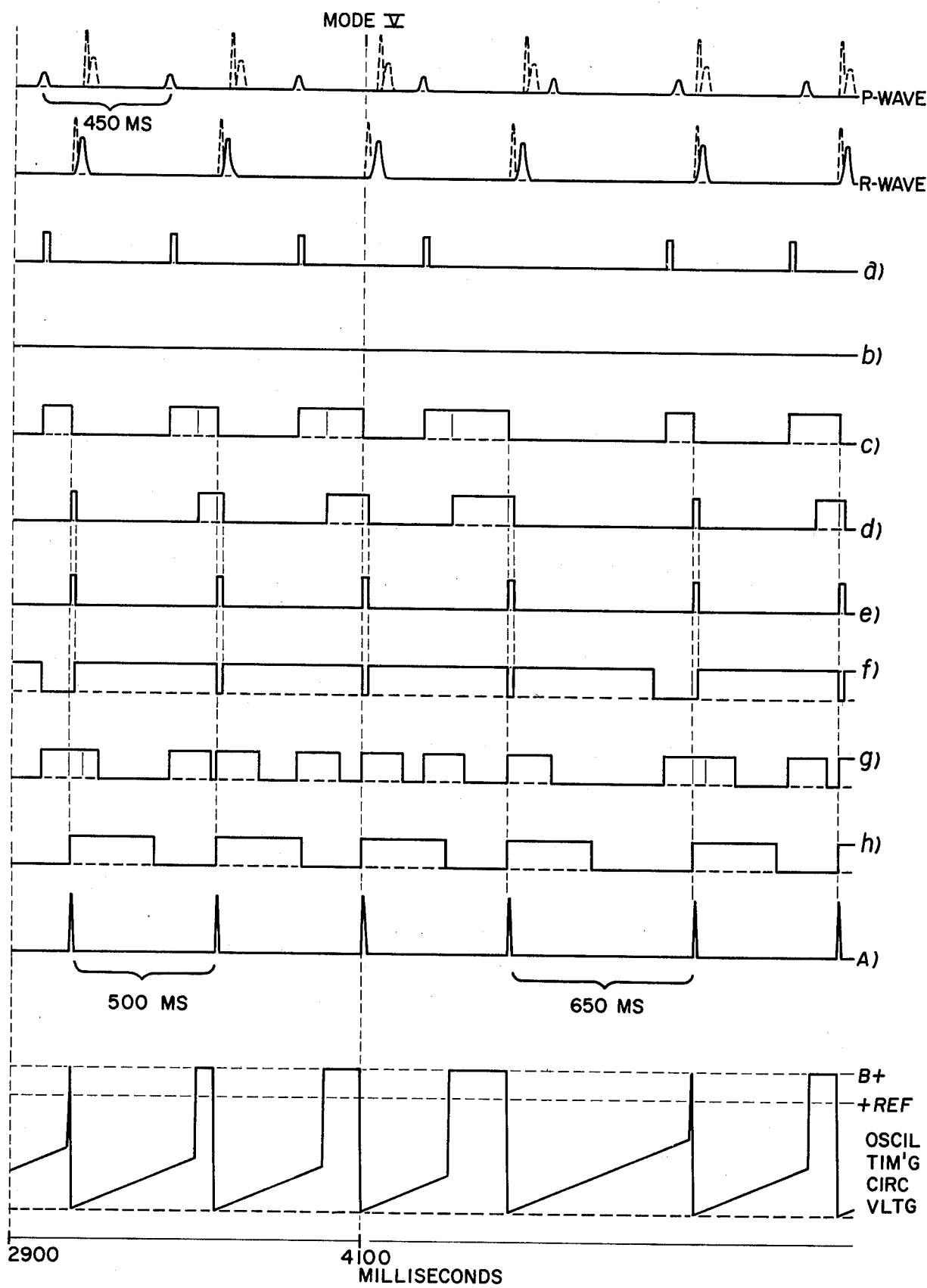

Referring now to FIGS. 4a and 4b, several modes of operation of the artificial cardiac pacer of my invention will be explained. In these figures, the P-wave and R-wave developed by the heart and picked up P-wave and R-waveelectrodes 18 and 14, respectively, the pacemaker artifact A, the sawtooth voltage wave form of the adjustable timing means of the oscillator, and wave forms developed at points a through h in the circuit of FIG. 2 are shown in consecutive points in time. The artifact A is shown in broken lines superimposed on the P-wave and R-wave wave forms to indicate that it is not picked up by the respective detectors. In the P-wave wave form, the R-wave is shown in broken lines, and conversely, in the R-wave wave form, the P-wave is shown in broken lines to indicate that they are not picked up by the respective detectors. The R-wave developed thereby, shown in broken lines in the P-wave wave form, is delayed in time to show that these signals would reach the atrial electrode after a time delayed transmission through the heart. The sawtooth wave form of the R-C oscillator voltage is developed at the junction of the R-C timing means of resistor R14 and capacitor C11 of FIG. 3 included within the oscillator 12. All of the wave forms depicted in FIGS. 4a and 4b are stylized for ease of illustration of the principle of operation of the invention and may not reflect actual amplitudes or polarities or shapes of the signals.

Five modes of operation of the circuits of FIGS. 2 and 3, as indicated at the tops of the wave form diagrams of FIGS. 4a and 4b, will be discussed. Mode I of the operation of the circuit represents the inhibited action thereof in the presence of normal heart activity. In Mode I, and with reference to FIG. 2, the P-wave signal is picked up by the atrial electrode 18 and is amplified by the P-wave detector 48 and appears as signal a on lead 62. The amplified P-wave signal a is applied to the Set input of memory 66, which responds thereto to produce the memory output signal on lead 68 depicted as c in FIG. 4. The memory output signal c is applied to the P-R time delay circuit 70 in FIG. 2 which, after a period of 100 ms, will TRIGGER, unless memory 66 is Cleared before the 100 ms elapses, the oscillator 12 into operation. The amplified P-wave signal a also is applied to the refractory circuit 58 which produces the refractory signal g that is applied to the sense amplifier 54. The refractory signal g has an invariable pulse width of 150 ms; however, the refractory period may be restarted during the 150 ms interval.

In the mode I situation, the ventricle of the heart contracts in response to the contraction of the atrium, the 100 ms of the time delay 70 elapses, and the natural R-wave signal is picked up by the ventricular lead 14 and amplified by the R-wave detector 24 to produce the amplified R-wave signal of wave form b. The amplified R-wave signal b is applied to the Clear input terminal of memory 66 to clear that memory thus terminating the memory output signal c. If we assume that the time interval between the production of wave forms a and b is 80 ms, the P-R time delay circuit 70 fails to TRIGGER the oscillator 12 as would be indicated in wave form d. With reference to the R-C oscillator curve of FIG. 4, it should be noted that the amplified R-wave signal b is applied to the RESET input of oscillator 12 to reset the voltage of the wave form to or near ground potential, therefore restarting the timing of the oscillator 12. Consequently, it may be seen that in Mode I, the artificial cardiac pacer circuit of FIGS. 2 and 3 is inhibited from producing a stimulating impulse due to the timely natural response of the ventricle to the atrial depolarization.

Mode II of operation of the pacemaker circuit of FIGS. 2 and 3 takes place when the patient's ventricle spontaneously depolarizes, without a prior depolarization of the atrium or the application of an electrical stimulus. Such an isolated, or ectopic R-wave, it it occurs before the timing circuit of the oscillator 12 fully times out, will reset the timing circuit of the oscillator to prevent the application of an artificial stimulus to the heart. This mode of operation of the pacer circuit of FIG. 2 is referred to as the ventricular inhibited mode of operation. When an ectopic R-wave is picked up by the ventricular electrode 14 and amplified in the R-wave detector 24, it is applied through conductor 39 to the RESET input of the oscillator 12, to the refractory circuit 34 of the R-wave sense amplifier 25, to the refractory circuit 58 of the P-wave sense amplifier 54, and to the Clear input of the memory 66. As shown in FIG. 4, at the instant the amplified R-wave signal $b$ is applied to the RESET input of oscillator 12, the voltage on capacitor C11 drops back again to 0 or ground. Also, although the P-wave detector 48 is tuned to reject all incoming wave forms except the P-wave, extra insurance is added by triggering the refractory circuit 58, so that the sense amplifier 54 is incapable of detecting any incoming signal for a period of 150 ms. Since the ventricular electrode 14 is closer to the ectopic source of depolarization in the ventricle than is the atrial 18, it follows that the R-wave depicted in dotted lines in the P-wave from in FIG. 4a will reach the atrial electrode after a certain time delay. Consequently, if due to the particular wave of the ectopic R-wave, the sense amplifier 54 could have possibly amplified it, this occurrence is prevented by triggering the refractory circuit 58 during that time period.

The third mode of operation of the artificial cardiac pacer of FIGS. 2 and 3 involves the situation where neither the atrium nor the ventricle of the heart depolarizes within a certain preset interval of the pulse generator timing means in the oscillator 12. This interval is preset, and it may conform to an interval of 1000 ms which corresponds to a heart beat rate of 60 beats per minute. Thus, if the heart beat rate of the patient's atrium and ventricle falls below 60 beats per minute, the artificial cardiac pacemaker is designed to respond to asynchronously stimulate the heart. This mode of operation may be called the demand mode, and it is illustrated in FIG. 4a in the time frame following the ectopic R-wave of Mode II. With reference to the R-C oscillator voltage wave form, it will be observed that at Mode II, the voltage was reduced to 0, and it steadily increases in the sawtooth pattern depicted until a predetermined reference voltage (+Ref.) is reached, whereupon the oscillator circuit produces the oscillator output signal $e$. The oscillator output signal $e$ is applied back to reset the oscillator 12 to reduce the voltage from the positive reference voltage level back to the 0 voltage level as depicted in FIG. 4a. Simultaneously, the signal $e$ is applied to the refractory circuits 34 and 58 and to Clear the memory 66. As depicted in the R-wave form of FIG. 4a, the oscillator output signal $e$ is amplified by the pulse amplifier 48 to produce the pacemaker stimulus or artifact A that is applied by the ventricular electrode 14 to depolarize the ventricle and produce the R-wave wave form. Since the oscillator output signal $e$ is applied to the refractory circuit 34 and 58, neither the R-wave detector 24 nor the P-wave detector 48 is capable of picking up the pacer artifact or the induced R-wave.

In Mode III it should be noted that following the generation of the oscillator output signal $e$ the rate limit circuit 50 responds to INHIBIT the oscillator 12 for 500 ms as indicated by the inhibit signal $f$.

Mode IV of operation of the artifical cardiac pacer circuit of FIGS. 2 and 3 involves the operation of the circuit in the P-wave synchronous mode; that is, a mode wherein the atrial depolarizations or P-waves occur at a rate exceeding the base rate of the oscillator 12 but are not effective to trigger the depolarization of the patient's ventricle due to a disorder in the heart's natural conduction system within the normal P-R interval, which in this instance is chosen to be 100 ms. It is also assumed in the explanation of this mode that the atrial rate is below the rate limit of 120 beats per minute, i.e., having an average interval exceeding 500 ms, established by the rate limit circuit 50.

Referring now to FIG. 2, at the start of Mode IV, the P-wave signal is detected and amplified in the P-wave detector 48, and the amplified P-wave signal $a$ Sets the memory 66 of the upper rate memory circuit 44. The Set state of the memory 66 is indicated by the wave form $c$ in FIG. 2. It should be noted that the P-wave has occurred after the termination of the refractory period of the sense amplifier 54 that was caused by the immediately preceding R-wave signal of Mode III. The memory output signal $c$ is applied to the P-R time delay circuit 70, and after a period of 100 ms, the P-R time delay circuit 70 triggers (wave form $d$) the production of an oscillator output signal $e$ by oscillator 12. With reference to the R-C oscillator voltage wave form in FIG. 4a at the instant the signal $d$ is depicted, full voltage is applied to the timing circuit means and the shape of the wave form changes. With voltage (B+) applied to the timing circuit means, the reference voltage level is rapidly reached and exceeded causing the oscillator 12 to produce the oscillator output signal $e$. The oscillator output signal $e$, in the manner described hereinbefore, resets the oscillator 12 and Clears the memory 66, thus terminating the oscillator output signal $e$ and the memory output signal $c$. The oscillator output signal $e$ is amplified by the pulse amplifier 48 and applied to the ventricular electrode 14, as artifact A and elicits the R-wave that follows the artifact A. In the same manner as described hereinbefore, the sense amplifier 54 is rendered refractory for its refractory period by the amplified P-wave signal $a$; and then 100 ms into the 150 ms refractory period, the oscillator output signal $e$ is applied to the refractory circuit 58 to restart the refractory period of the sense amplifier 54 as shown in wave form $g$. Upon the production of the oscillator output signal $e$ the rate limit circuit 50 again inhibits the oscillator 12 for 500 ms and renders sense amplifier 25 refractory for 300 ms.

All of the above described modes of operation are known from the prior art. In accordance with my invention the pacemaker circuit operates in a fifth mode that advantageously realizes a stable upper rate limit for the operation of a synchronous pacemaker.

Turning now to Mode V, depicted in FIG. 4b, it will be assumed that the atrial, P-wave rate increases above 120 beats per minute. As depicted in FIG. 4b, this means that the interval between P-waves decreases below 500 ms. For convenience of illustration, the P-wave interval is assumed to go from just above 500 ms at the left in the diagram to about 450 ms (133 beats per minute) through the remaining depicted intervals. It will also be assumed that the Mode IV rate limit signal $f$ is just timing out at the first P-wave (counted from the left) is detected. Again, as in the Mode IV operation, an artifact A is produced after 100 ms from the detection and amplification of the P-wave. The rate limit circuit is restarted to inhibit the oscillator for 500 ms and the oscillator timing circuit voltage restarts.

The second P-wave arrives about 450 ms after the first P-wave, and P-wave detector 48 responds to produce the amplified P-wave signal *a*, because the refractory circuit 58 has already timed out. Signal *a* Sets the memory circuit 66 to produce the memory output signal *c*. After 100 ms, the oscillator 12 is triggered. However, the oscillator is incapable of responding for 50 ms, and, as shown in the timing circuit voltage wave form, the timing circuit voltage remains near B+ until the full 500 ms operation of the rate limit circuit 50 times out. As soon as the oscillator 12 is no longer inhibited, it is triggered to produce the oscillator output signal *e* and the pacemaker artifact A. As shown in FIG. 4*b*, at the time that the oscillator output signal *e* is produced, the P-wave refractory circuit 58 is fully timed out; consequently, it is restarted at that instant.

The third and fourth P-waves elicit a similar response from the pacemaker circuit of FIGS. 2 and 3. It should be noted though, that the P-R intervals are widening until the fourth R-wave almost corresponds in time with the fifth P-wave. Because of the chance that the natural P-wave and the driven R-wave could occur simultaneously, and because the P-wave detector 48 might not be able to distinguish the two unless perhaps, the detector filter circuits could be custom tuned for each patient, the P-wave detector 48 is rendered refractory both by the amplified P-wave *a* and by the oscillator output signal *e*.

Consequently, when the fifth P-wave occurs, the P-wave detector 48 is refractory due to the previous oscillator output signal *e*. Therefore, the upper rate memory circuit 44 is not Set by the fifth P-wave, and the pacemaker is inhibited until the sixth P-wave occurs. As shown in FIG. 4*b*, the pacemaker has delivered stimulating artifacts A at a constant interval of 500 ms through the fourth P-wave. But the interval between the fourth artifact A and the next artifact A is wider—approaching 650 ms—representing the skipped P-wave. At the sixth P-wave, however, all refractory and rate limit circuits are dormant, and the R-wave follows in the 100 ms interval—in the identical fashion with the response of the pacemaker circuit to the first depicted P-wave.

Consequently, as can be seen from FIG. 4*b*, in its fifth mode of operation, the pacemaker circuit of my invention responds to a P-wave rate exceeding a predetermined upper limit—120 beats per minute—to stabilize the rate at approximately the upper limit.

Periodically the rate drops for one beat to a lower rate that still substantially exceeds the base rate of the oscillator circuit or half the actual P-wave rate. The average pacemaker rate equals the upper rate limit when it in turn is equaled by the P-wave rate and then gradually drops slightly as the P-wave rate continues to climb. It should be noted that whenever a signal *b* is provided by sense amplifier 25 or a signal *e* is provided by oscillator 12, refractory circuit 34 provides a 300 ms. pulse signal *h* to render sense amplifer 25 refractory.

Physiologically speaking, the upper rate stabilization of synchronous pacemaker operation achieved by my invention has the advantage that the patient's cardiac output is not abruptly halved. Although the average pacemaker rate stabilizes near the upper rate as the natural P-wave rate increases, the concurrent stabilization in cardiac output will itself tend to bring down the P-wave rate relatively slowly as the patient then moderates his activity. The upper rate limit chosen for a particular patient can be selected to fit his expected level of physical activity. With my invention, all patients will benefit by the added comfort and safety from physical harm during periods of strenuous activity or mental stress that raise their cardiac output requirements.

From a reliability and physiological viewpoint, the periodic re-establishment of constant timed synchronism (the 100 ms delay) of the pulse generator stimulus with the selectively detected P-waves, when the heart's atrial rate exceeds the upper or maximum pacing rate, allows the physician to verify, from an ECG strip, that the implanted pacemaker is functioning correctly and is not merely running asynchronously at the upper pacing rate. Also, from an engineering viewpoint, the operation of the pacemaker circuit as hereinbefore described, in rendering the P-wave detector circuit refractory following both a detected P-wave, a detected R-wave and a pulse generator output or reset signal recognizes that the P-wave detector sensing circuit would have difficulty distinguishing between a natural P-wave and a pacemaker driven R-wave that closely coincides in time with the natural P-wave, as is bound to occur (in Mode V) when the natural atrial rate exceeds the upper pacing rate.

Having thus described my invention with particularity with reference to the preferred form, it will be obvious to those skilled in the art, after understanding my invention, that other changes and modifications may be made therein without departing from the spirit and scope of the invention, and I aim in the appended claims to cover such changes and modifications as are within the scope of the invention.

What I claim is:

1. In a synchronous heart pacemaker, including:
   means for selectively detecting natural electrical heart signals;
   means for generating an artificial pacing stimulus in timed synchronism with the detected heart signal; and
   means for applying the generated pacing stimulus to the heart to elicit a responsive heart beat; the improvement for stabilizing the synchronous pacing rate at an average rate approaching but not exceeding the upper pacing rate comprising:
   means for inhibiting the generation of a subsequent pacing stimulus for a predetermined time interval corresponding to an upper pacing rate; and
   means for varying the time elapsed from the detection of electrical heart signals recurring at a rate exceeding the upper pacing rate and the synchronous generation of artificial pacing stimulus to include the predetermined time interval.

2. The synchronous heart pacemaker of claim 1 further comprising:
   means for periodically interrupting the selective detection of natural electrical heart signals recurring at a rate exceeding the upper pacing rate so that the generation of a subsequent pacing stimulus is in timed synchronism with the detected heart signal.

3. In a method of operation of a synchronous heart pacemaker, comprising the steps of:
   selectively detecting natural electrical heart signals;

generating an artificial pacing stimulus in timed synchronism with the detected heart signal; and applying the generated pacing stimulus to the heart to elicit a responsive heart beat;

the improvement for stabilizing the synchronous pacing rate at an average rate approaching but not exceeding the upper pacing rate comprising the steps of:

inhibiting the generation of a subsequent pacing stimulus for a predetermined time interval corresponding to an upper pacing rate; and varying the time elapsed from the detection of electrical heart signals recurring at a rate exceeding the upper pacing rate and the synchronous generation of artificial pacing stimulus to include the predetermined time interval.

4. The method of claim 3 further comprising the step of:

inhibiting the detection of natural electrical heart signals for a further predetermined time interval upon the generation of a pacing stimulus so that the synchronous generation of the artificial pacing stimulus at the upper pacing rate is periodically interrupted for one pacing cycle to re-establish the time synchronism of generation of the artificial pacing stimulus.

5. The method of claim 3 further comprising the step of:

periodically interrupting the selective detection of natural electrical heart signals recurring at a rate exceeding the upper pacing rate so that the generation of a subsequent pacing stimulus is in timed synchronism with the detected heart signal.

6. In a synchronous artificial cardiac pacemaker comprising pulse generator means operable to generate electrical pacing pulses applicable to the patient's heart to elicit a responsive heart beat in timed synchronism with a natural electrical heart signal detectable from the patient's heart at a synchronous rate extending between a lower, base pacing rate and an upper maximum pacing rate including timing circuit means controlling the generation of the pacing pulses at the lower, base pacing rate upon the failure of the pacemaker to detect such natural heart signals within a maximum time interval, the improvement comprising:

upper rate limit circuit means for establishing the maximum pacing rate by inhibiting the generation of the pacing pulses for a predetermined minimum time interval following the generation of each such pacing pulse;

means for varying the time elapsed from the detection of electrical heart signals recurring at a rate exceeding the maximum pacing rate and the synchronous generation of artificial pacing pulses to include the predetermined minimum time interval; and means for periodically interrupting the selective detection of natural electrical heart signals recurring at a rate exceeding the upper pacing rate so that the generation of a subsequent pacing pulse is in timed synchronism with the detected heart signal.

7. The synchronous artificial cardiac pacemaker of claim 6 further comprising:

a first electrode coupled to said pulse generator means, said first electrode being adapted to be operatively connected to a patient's heart on or in the ventricle thereof to transmit the artificial pacing pulses to the patient's ventricle and to pick up natural ventricular electrical signals; and reset circuit means coupled to said timing circuit means and said first electrode and responsive to a ventricular electrical signal to restart the maximum time interval and prevent the pulse generator from stimulating the heart for the maximum time interval.

8. The synchronous artificial cardiac pacemaker of claim 7 further comprising:

a second electrode coupled to said pulse generator, said second electrode being adapted to be operatively connected to a patient's heart on or in the atrium thereof to pick up natural atrial electrical signals; and trigger circuit means coupled to said pulse generator means and said second electrode and responsive to the atrial electrical signals to trigger said pulse generator means into generating a pacing pulse synchronously with a detected atrial electrical signal.

9. The synchronous artificial cardiac pacemaker of claim 8, wherein said periodically interrupting means further comprises:

signal responsive means coupled to said second electrode and said trigger circuit means and responsive to atrial electrical signals picked up by said second electrode for rendering said trigger circuit means operable; and refractory circuit means coupled to said signal responsive means and said pulse generator means and responsive to a generated pacing pulse to inhibit said signal responsive means from responding to atrial electrical signals for a predetermined refractory time period so that as the synchronous pacing time interval increases as the atrial heart rate increases, an atrial signal will fall within the refractory time period and will not be sensed to produce a pacing pulse.

10. The synchronous artificial cardiac pacemaker of claim 6 further comprising:

a second electrode coupled to said pulse generator, second electrode being adapted to be operatively connected to a patient's heart on or in the atrium thereof to pick up natural atrial electrical signals; and trigger circuit means coupled to said pulse generator means and said second electrode and responsive to the atrial electrical signals to trigger said pulse generator means into generating a pacing pulse synchronously with a detected atrial electrical signal.

11. The synchronous artificial cardiac pacemaker of claim 10 further comprising:

time delay circuit means coupled to said second electrode and said trigger circuit means and adapted to respond to each detected atrial electrical signal for causing said trigger circuit to trigger said pulse generator means into generating a pacing pulse in timed synchronism, after an atrial-ventricular time delay, with the detection of the atrial electrical signal; and said varying means further comprises: p1 memory circuit means coupled to said second electrode and said time delay circuit means and responsive to the atrial electrical signal for maintaining the response of said time delay circuit for a time period exceeding the elapse of the predetermined time interval of said upper rate limit circuit means, so that said trigger circuit means will trigger said pulse generator into generating a pacing pulse in synchronism with the atrial electrical activity of the heart.

12. An atrial synchronous artificial cardiac pacemaker comprising:
pulse generator means operable to generate electrical pacing pulses applicable to a patient's ventricle to elicit a responsive contraction of the heart in synchronism with a natural atrial electrical signal detectable from the patient's heart at a synchronous rate extending between a lower, base pacing rate and an upper maximum pacing rate; said pulse generator means including timing circuit means controlling the generation of the pacing pulses at the lower, base pacing rate upon the failure of the pacemaker to detect atrial or ventricular electrical signals within a maximum time interval, upper rate limit circuit means for establishing the maximum pacing rate by inhibiting the generation of the pacing pulses for a predetermined minimum time interval following the generation of each such pacing pulse; reset circuit means coupled to said timing circuit means and adapted to restart the maximum timing interval in response to atrial electrical signals, and trigger circuit means coupled to said pulse generator means and operable to trigger said pulse generator means into generating a pacing pulse independently of said timing circuit means;

first and second electrodes coupled to said pulse generator means, said first electrode being adapted to be operatively connected to a patient's heart on or in the ventricle thereof to transmit the artificial pacing pulses to the patient's ventricle and to pick up natural ventricular electrical signals, said second electrode being adapted to be operatively connected to a patient's heart on or in the atrium thereof to pick up natural atrial electrical signals;

first signal responsive means coupled to the first electrode and responsive to ventricular electrical signals picked up by the first electrode for producing a first signal;

second signal responsive means coupled to the second electrode and responsive to atrial electrical signals picked up by the second electrode for producing a second signal;

circuit means coupled to said first signal responsive means and said reset circuit means and responsive to the first signal to reset the timing circuit means to restart said maximum timing interval between pacing pulses;

time delay circuit means coupled to said trigger circuit means and adapted to respond to each second signal for triggering said pulse generator means into generating a pacing pulse in synchronism, after an atrial-ventricular time delay, with the detection of the atrial electrical signal; and memory circuit means having input means coupled to said first and second signal responsive means and output means coupled to said time delay circuit means, said memory circuit means responsive to the second signal for maintaining the second signal at said time delay circuit for a time period exceeding the elapse of the predetermined time interval of said upper rate limit circuit means, whereby the pulse generator operates to produce a pacing pulse in synchronism with atrial electrical signals detected from the atrium but at an average rate not exceeding the maximum pacing rate.

13. The synchronous artificial cardiac pacemaker of claim 12 further comprising:
refractory circuit means coupled to said second signal responsive means and said pulse generator means and responsive to a generated pacing pulse to inhibit said second signal responsive means to periodically interrupt the production of the second signal when the atrial electrical signal recurs at a rate exceeding the maximum pacing rate, so that the predetermined minimum time interval of the upper rate limit circuit means will elapse before a succeeding atrial electrical signal is picked up by said second electrode.

14. The synchronous artificial cardiac pacemaker of claim 12 wherein:
said input means of said memory circuit means is coupled to said circuit means; and
said memory circuit means is responsive to the first signal for removing the second signal at said time delay circuit on the occurrence of the first signal.

15. An atrial synchronous cardiac pacemaker for pacing the ventricle portion of the heart at a rate in synchronism with the natural contraction of the atrium portion of the heart, but at a rate above a lower rate limit and below an upper rate limit, said pacemaker comprising:
an oscillator responsive to a trigger signal for generating an electrical pulse signal adapted to be applied over a lead to the ventricle portion of the heart to elicit a responsive heart beat, said oscillator further being operable to generate said pulse signal upon the absence of any trigger signal for a designated time period, said oscillator including rate limit means for preventing said pulse signals from being generated at a rate exceeding an upper rate limit;
sensing means responsive to the occurrence of a cardiac signal caused by the contraction of the atrium of the heart for providing a signal each time said atrium contracts, said sensing means further including means for inhibiting the response by said sensing means to an atrium contraction caused signal which occurs during a fixed time, less than said designated time, after the provision of each pulse signal; and
memory means, which in response to said sensing means signal, provides said trigger signal to said oscillator until said pulse signal is generated, said memory means being reset each time a pulse signal is generated and set each time a sensing means signal is provided.

16. The invention according to claim 15 wherein said pacemaker further comprises:
second sensing means responsive to a cardiac signal caused by the contraction of the ventricle of the heart for providing a second sensing means signal each time said ventricle naturally contracts; and
means for providing said second sensing means signal to reset said memory, to inhibit the response by said first sensing means for said fixed time and to reset said oscillator to commence said designated time period.

17. The invention according to claim 15 wherein said memory means include means for delaying the provision of said trigger signal to said oscillator for a selected time after the provision of said sensing means signal.

* * * * *